US009089281B2

(12) United States Patent
Yuasa et al.

(10) Patent No.: US 9,089,281 B2
(45) Date of Patent: Jul. 28, 2015

(54) OPTICAL TOMOGRAPHIC IMAGING APPARATUS

(75) Inventors: Takashi Yuasa, Sagamihara (JP); Kenichi Saito, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 293 days.

(21) Appl. No.: 13/132,101

(22) PCT Filed: Dec. 24, 2009

(86) PCT No.: PCT/JP2009/071861
§ 371 (c)(1),
(2), (4) Date: Jun. 1, 2011

(87) PCT Pub. No.: WO2010/074321
PCT Pub. Date: Jul. 1, 2010

(65) Prior Publication Data
US 2011/0242487 A1   Oct. 6, 2011

(30) Foreign Application Priority Data

Dec. 26, 2008   (JP) .................................. 2008-332245
May 22, 2009   (JP) .................................. 2009-124105

(51) Int. Cl.
*A61B 3/14*   (2006.01)
*A61B 3/10*   (2006.01)
(Continued)

(52) U.S. Cl.
CPC ............... *A61B 3/102* (2013.01); *A61B 5/0059* (2013.01); *A61B 5/0066* (2013.01);
(Continued)

(58) Field of Classification Search
CPC .... A61B 3/102; A61B 5/0066; A61B 5/0073; A61B 3/14; A61B 3/12; A61B 5/6852; A61B 5/7257; A61B 3/1225; A61B 5/0059; A61B 3/1025; A61B 5/0088; A61B 3/0058; A61B 3/1005; A61B 3/1015; A61B 3/113
USPC ......... 351/200, 205–206, 221–222; 359/204.1–204.4, 370, 371; 356/450, 356/477, 479, 496, 497; 600/425
See application file for complete search history.

(56) References Cited

U.S. PATENT DOCUMENTS 5,465,147 A      11/1995   Swanson
2007/0258095 A1  11/2007   Olivier et al.
(Continued)

FOREIGN PATENT DOCUMENTS

EP   1870030 A1   12/2007
JP   2875181 B2    3/1999
(Continued)

OTHER PUBLICATIONS

International Preliminary Report on Patentability dated Jun. 29, 2011, in counterpart International Application No. PCT/JP2009/071861.
(Continued)

*Primary Examiner* — Scott J Sugarman
*Assistant Examiner* — Brandi Thomas
(74) *Attorney, Agent, or Firm* — Fitzpatrick, Cella, Harper & Scinto

(57) ABSTRACT

Provided is an optical tomographic imaging apparatus that can suppress variations of resolution, sensitivity, and the like and reduce the number of components for equalizing optical properties so that cost can be reduced, in a case of an OCT apparatus using a plurality of lights. The optical tomographic imaging apparatus for obtaining a tomographic image of an object includes an optical property adjusting unit for adjusting an optical property of at least one light of measurement lights, reference lights, and interference lights each comprised of a plurality of lights. The optical property adjusting unit is shared by each group including measurement lights having substantially the same distance from an optical axis of an irradiation optical system among the measurement lights comprised of a plurality of lights.

18 Claims, 6 Drawing Sheets

(51) Int. Cl.
  *A61B 5/00* (2006.01)
  *G01N 21/47* (2006.01)
  *G01B 9/02* (2006.01)

(52) U.S. Cl.
  CPC ....... *G01B 9/02012* (2013.01); *G01B 9/02019* (2013.01); *G01B 9/02027* (2013.01); *G01B 9/02044* (2013.01); *G01B 9/02058* (2013.01); *G01B 9/02091* (2013.01); *G01N 21/4795* (2013.01); *G01B 2290/45* (2013.01)

(56) References Cited

U.S. PATENT DOCUMENTS

| | | | |
|---|---|---|---|
| 2008/0088852 A1* | 4/2008 | Rogers et al. | 356/497 |
| 2008/0117431 A1* | 5/2008 | Teramura | 356/511 |
| 2008/0123092 A1* | 5/2008 | Hatori | 356/300 |
| 2008/0259275 A1 | 10/2008 | Aoki et al. | |
| 2009/0021746 A1 | 1/2009 | Toida et al. | |
| 2011/0249236 A1 | 10/2011 | Saito et al. | |
| 2011/0279778 A1 | 11/2011 | Saito | |

FOREIGN PATENT DOCUMENTS

| | | |
|---|---|---|
| JP | 2006-195240 A | 7/2006 |
| JP | 2007-151631 A | 6/2007 |
| WO | 2006/054116 A2 | 5/2006 |
| WO | 2006-054975 A2 | 5/2006 |

OTHER PUBLICATIONS

International Search Report and Written Opinion of the International Searching Authority mailed May 17, 2010, in International Application No. PCT/JP2009/071861.

Jun. 26, 2013 Chinese Official Action in Chinese Patent Appln. No. 200980152988.0.

Mar. 12, 2015 European Communication in European Patent Appln. No. 09801568.8.

* cited by examiner

OPTICAL TOMOGRAPHIC IMAGING APPARATUS

TECHNICAL FIELD

The present invention relates to an optical tomographic imaging apparatus, and more particularly, to an optical tomographic imaging apparatus that is used for ophthalmological examination, tomographic observation of skin, wall surface tomographic photographing of a digestive organ or a circulatory organ with an endoscope or a catheter constituted of the optical tomographic imaging apparatus, or the like.

BACKGROUND ART

In recent years, an optical coherence tomographic imaging method and an optical coherence tomographic imaging apparatus, to which a low coherence interferometer technology or a white light interferometer technology is applied, are practically used.

In particular, an optical tomographic imaging apparatus that performs an optical coherence tomography (OCT) utilizing interference of multi-wavelength light can obtain a tomographic image of a sample with high resolution.

Therefore, in the ophthalmological field, an optical coherence tomographic apparatus is becoming an indispensable apparatus for obtaining a tomographic image of a fundus or a retina.

In addition to the ophthalmological application, the optical coherence tomographic apparatus has also been used for tomographic observation of skins, wall surface tomographic photographing of a digestive organ or a circulatory organ with an endoscope or a catheter constituted of the apparatus, or the like. Hereinafter, the optical coherence tomographic apparatus is referred to as an OCT apparatus.

The OCT apparatus utilizes characteristics of light to enable measurement with high resolution compared with an ultrasonic tomographic diagnosis apparatus or the like, and thus can perform fine measurement but requires a long measurement time for measuring a wide region.

In order to cope with the above-mentioned problem, there is known a method of using a plurality of measurement lights and deviding a wide region into a plurality of regions to be measured with the individual lights simultaneously.

Japanese Patent No. 2875181 discloses an optical coherence tomographic imaging apparatus, which uses a plurality of light sources and photosensors so that the individual light sources and photosensors are associated with each other by a common imaging optical system.

In addition, Japanese Patent Application Laid-Open No. 2006-195240 discloses an apparatus that splits one light into a plurality of condensed lights by a micro lens array so as to perform interference measurement.

In structuring the OCT apparatus using a plurality of lights, the following problems can occur, which are not examined in the above-mentioned conventional examples disclosed in Japanese Patent No. 2875181 or Japanese Patent Application Laid-Open No. 2006-195240.

Specifically, in structuring the OCT apparatus using a plurality of lights, the individual lights actually follow different optical paths. Therefore, influence of an optical system including an optical path length, light quantity, wavelength dispersion, aberration and a signal processing step are different among the individual lights.

These factors cause variations of contrast, resolution, sensitivity, and the like in OCT images obtained by the individual lights, and hence it is necessary to reduce the variations.

In order to reduce the variations, it is necessary to equalize the influence on the individual lights, which increases the number of components and cost in proportion to the number of lights.

DISCLOSURE OF THE INVENTION

The present invention has been made in order to solve the above-mentioned problem and has an object to provide, when structuring the OCT apparatus using a plurality of lights, an optical tomographic imaging apparatus that can suppress variations of resolution, sensitivity, and the like and reduce the number of components for equalizing optical properties so that cost can be reduced.

The present invention provides an optical tomographic imaging apparatus having the following structure.

The optical tomographic imaging apparatus of the present invention splits a light emitted from a light source into a plurality of lights, which are further split into measurement lights and reference lights.

The measurement lights comprised of a plurality of lights are directed to an object to be measured via an irradiation optical system for irradiating different positions on the object with the measurement lights. The reference lights comprised of a plurality of lights are directed to reference mirrors. The measurement lights comprised of a plurality of lights are reflected or scattered by the object to become return lights. The reference lights comprised of a plurality of lights reflected by the reference mirrors and the return lights are combined to generate interference lights, which are processed by a spectral processing portion. In this manner, the optical tomographic imaging apparatus obtains a tomographic image of the object. The optical tomographic imaging apparatus includes an optical property adjusting unit for adjusting optical properties of at least one light of the measurement lights, the reference lights, and the interference lights each comprised of a plurality of lights.

The optical property adjusting unit is shared by each group including measurement lights having substantially the same distance from an optical axis of the irradiation optical system among the measurement lights comprised of a plurality of lights.

Further, the optical tomographic imaging apparatus of the present invention splits a light emitted from a light source into a plurality of lights, which are further split into measurement lights and reference lights each comprised of the plurality of lights.

The measurement lights comprised of a plurality of lights are directed to an object to be measured via an irradiation optical system for irradiating different positions on the object with the measurement lights. The reference lights comprised of a plurality of lights are directed to reference mirrors. The measurement lights comprised of a plurality of lights are reflected or scattered by the object to become return lights. The reference lights comprised of a plurality of lights reflected by the reference mirrors and the return lights are combined to generate interference lights, which are processed by a spectral processing portion. In this manner, the optical tomographic imaging apparatus obtains a tomographic image of the object. The optical tomographic imaging apparatus includes an optical property adjusting unit for adjusting optical properties of at least one light of the measurement lights, the reference lights, and the interference lights each comprised of a plurality of lights.

The optical property adjusting unit varies depending on a distance from an optical axis of the irradiation optical system among the measurement lights comprised of a plurality of lights.

Further, the optical tomographic imaging apparatus of the present invention obtains tomographic images of an object by directing measurement lights comprised of a plurality of lights to the object to be measured via an irradiation optical system for irradiating different positions on the object with the measurement lights and processing at a spectral processing portion interference lights generated by combining at a combining unit return lights of the measurement lights comprised of a plurality of lights reflected or scattered by the object and reference lights comprised of a plurality of lights, the apparatus including an optical property adjusting unit for adjusting an optical property of at least one light of the measurement lights, the reference lights, and the interference lights each comprised of a plurality of lights.

In the optical tomographic imaging apparatus, the optical property adjusting unit varies depending on a distance from an optical axis of the irradiation optical system among the measurement lights comprised of a plurality of lights.

According to the present invention, when structuring the OCT apparatus using a plurality of lights, the optical tomographic imaging apparatus can be realized, which can suppress variations of resolution, sensitivity, and the like and reduce the number of components for equalizing optical properties so that cost can be reduced.

Further features of the present invention will become apparent from the following description of exemplary embodiments with reference to the attached drawings.

BEST MODE FOR CARRYING OUT THE INVENTION

Next, an embodiment of the present invention is described.

In this embodiment, an optical tomographic imaging apparatus is structured as follows, to thereby suppress variations of resolution, sensitivity, and the like and reduce the number of components for equalizing optical properties so that cost can be reduced.

In the fundamental structure of the optical tomographic imaging apparatus, a light emitted from a light source is split into a plurality of lights, which are further split into measurement lights and reference lights.

The measurement lights comprised of a plurality of lights are directed to an object to be measured via an irradiation optical system for irradiating different positions on the object with the measurement lights. The reference lights comprised of a plurality of lights are directed to reference mirrors. The measurement lights comprised of a plurality of lights are reflected or scattered by the object to become return lights. The reference lights comprised of a plurality of lights reflected by the reference mirrors and the return lights are combined to generate interference lights, which are processed by a spectral processing portion. In this manner, a tomographic image of the object is obtained.

The optical tomographic imaging apparatus includes an optical property adjusting unit for adjusting optical properties of at least one light of the measurement lights, the reference lights, and the interference lights each comprised of a plurality of lights.

In this case, the optical property adjusting unit is shared by each group including measurement lights having substantially the same distance from an optical axis of the irradiation optical system among the measurement lights comprised of a plurality of lights.

Hereinafter, a specific structure thereof is described further with reference to the attached drawings.

Figure 1:
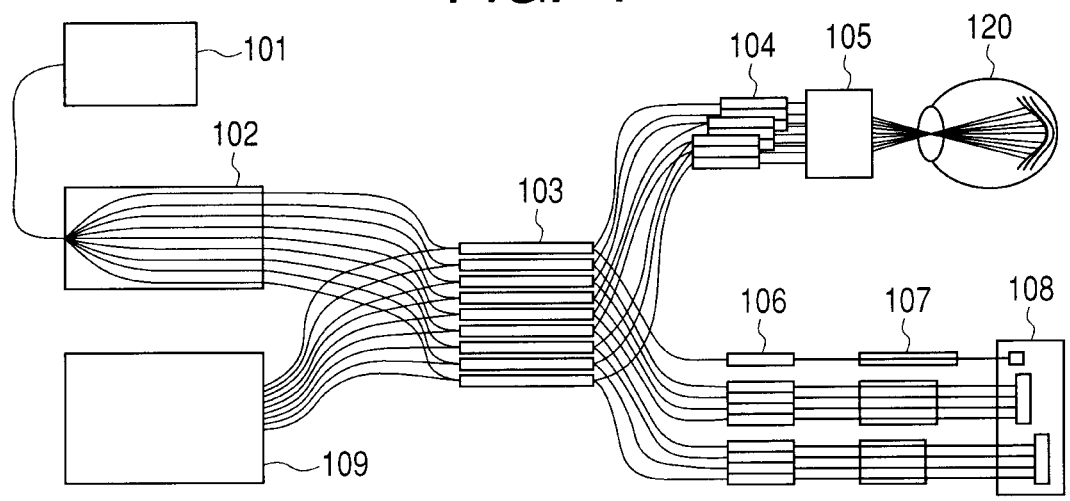
FIG. 1 is a diagram illustrating a structure of an optical tomographic imaging apparatus according to an embodiment and Embodiment 1 of the present invention.

FIG. 1 is a diagram illustrating a structure of the optical tomographic imaging apparatus according to this embodiment.

The optical tomographic imaging apparatus illustrated in FIG. 1 includes a low coherence light source 101, a fiber beam splitter 102, a fiber coupler 103, a fiber collimator 104, and an irradiation optical system 105.

The optical tomographic imaging apparatus further includes a fiber collimator 106, dispersion compensation glasses 107, a reference mirror group 108, and a spectral processing portion 109, and an object to be measured is represented by reference numeral 120.

In the optical tomographic imaging apparatus of this embodiment, a light emitted from the low coherence light source 101 is split into nine lights by the fiber beam splitter 102. Each light is split into a measurement light and a reference light by the fiber coupler 103.

The measurement lights are converted to parallel lights by the fiber collimator 104 and are directed by the irradiation optical system 105 to different measurement positions on the object 120.

Each scattered light generated at the measurement position is directed again by the irradiation optical system 105 and the fiber collimator 104 to the fiber and is combined with the reference light by the fiber coupler 103 so that an interference light is generated.

On the other hand, the reference lights are converted to parallel lights by the fiber collimator 106, which pass through dispersion compensation glasses 107 for dispersion compensation, are reflected by the reference mirror group 108, and return to the fiber coupler 103.

The dispersion compensation glasses 107 is provided for compensating for a wavelength dispersion difference between the measurement light side and the reference light side.

The interference light generated by the fiber coupler 103 enters the spectral processing portion 109, and then each of the nine combined lights is spectrally-measured and is converted into OCT signals through signal processing steps of performing a Fourier transformation process and the like.

Figure 2:
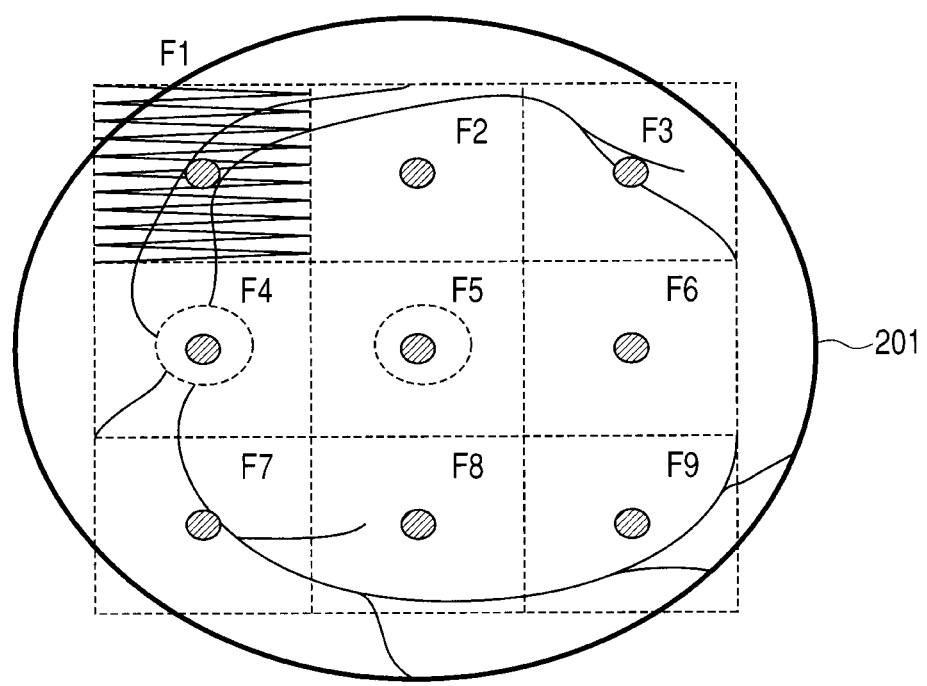
FIG. 2 is a diagram illustrating an arrangement of scanning lights in embodiments of the present invention.

The measurement light directed by the irradiation optical system 105 is directed to nine regions F1 to F9 on a measurement curved surface 201 as illustrated in FIG. 2 so as to scan the regions.

In this case, with respect to the region F5 on the optical axis of the irradiation optical system 105 as a center, regions having the same distance from the optical axis have the same optical property.

In other words, the regions can be separated into three groups of {F5}, {F2, F4, F6, F8}, and {F1, F3, F7, F9}. In each group, the length of the dispersion compensation glass 107 can be the same.

Therefore, it is sufficient to prepare three types of the dispersion compensation glasses 107 as illustrated in FIG. 1, and corresponding to that, positions of the reference mirror group 108 should be combined in three types, i.e., the number of groups.

In this way, by classifying the scanning lights in accordance with the distance from the optical axis of the optical system, ones having substantially the same optical property can be put into one group.

In the above-mentioned structure of this embodiment, the lights of the same group pass through the same reference optical system. Therefore, variations among the nine OCT signals can be reduced while minimizing an increase of the number of components for equalizing optical properties of the individual lights. In addition, the optical tomographic imaging apparatus having the above-mentioned structure according to this embodiment can be used for observation of a fundus or skin, or observation of a bio-organ using an endoscope, or various diagnosis apparatuses or inspection apparatuses as well as for industrial quality control.

Here, as another embodiment, it is possible to store a program for causing a computer to execute an imaging method using the optical tomographic imaging apparatus according to the above-mentioned embodiment, in a computer-readable storage medium (e.g., flexible disc, hard disk, optical disc, opto-magnetic disk, CD-ROM, CD-R, magnetic tape, non-volatile memory card, ROM, EEPROM, Blu-ray disc, or the like). In addition, as still another embodiment, it is possible to use a program for causing a computer to execute the imaging method using the above-mentioned optical tomographic imaging apparatus.

EMBODIMENTS

Hereinafter, embodiments of the present invention are described.

Embodiment 1

In Embodiment 1, a structural embodiment of the optical tomographic imaging apparatus to which the present invention is applied is described. This embodiment uses the above-mentioned optical tomographic imaging apparatus illustrated in FIG. 1 as a fundamental structure.

In addition, in this embodiment, a retina of an eye is used as the object 120 to be measured.

As the low coherence light source 101, an SLD light source having an output power of 20 mW, a center wavelength of 840 nm, and a wavelength width of 45 nm is used.

The light emitted from the light source is split equally into nine lights by a one-to-nine fiber beam splitter 102.

The nine lights are split into respective measurement lights and reference lights by nine 50:50 fiber couplers 103.

The measurement lights are converted to parallel lights by the fiber collimator 104 and applied onto a retina 120 of an eye by the irradiation optical system 105 constituted of a galvano-scanner, a scan lens, and an ocular lens.

As illustrated in FIG. 2, the region that is scanned by each light on the fundus image 201 is adjusted so that one light corresponds to each of nine regions F1 to F9 that are divided into a grid.

Each light conducts raster-scanning on each of the divided regions so as to obtain three-dimensional OCT data.

In addition, the nine reference lights are converted to parallel lights by the fiber collimator 106 and reflected by the reference mirror group 108 through the dispersion compensation optical system 107 so as to return to the fiber coupler 103.

The ocular lens used in the irradiation optical system 105 has a wide angle of view that is capable of scanning the fundus by a total angle of 30 degrees.

In order to eliminate wave aberration, color aberration, and the like, the ocular lens is a combination lens of difference glass materials.

Therefore, the thickness of each glass material varies between a vicinity of the optical axis and a periphery of the lens, and hence wavelength dispersion of the light also varies between the case where the light passes through the vicinity of the optical axis and the case where the light passes through the periphery of the lens. It was found from calculation using the lens data of the used lens that the wavelength dispersion value of the lens material becomes larger by approximately 5% in the periphery of the lens compared with the vicinity of the optical axis.

Therefore, the length of the BK7 glass 107 for dispersion compensation should be changed by 5% between the light for scanning the region F1 and the light for scanning the region F5.

Here, considering that optical property of a lens system is symmetric with respect to the optical axis, lights at the same distance from the optical axis have the same dispersion value.

Therefore, three types of the BK7 glasses 107 for dispersion compensation are sufficient for three groups of {F5}, {F2, F4, F6, F8}, and {F1, F3, F7, F9}. In this embodiment, based on a difference of the dispersion value from the measurement light side, three types of 200 mm, 195 mm, and 190 mm are used. In addition, the reference mirror group 108 has a structure including three mirrors placed on an electric linear movement stage.

If optical path length differences occurs between the measurement lights and the reference lights, the three mirrors are adjusted with positional differences thereamong in accordance with the lengths of the BK7 glasses 107 of the three groups so that the optical path lengths become substantially the same between the measurement light and the reference light. The optical path length in the glass becomes shorter when passing through the BK7 glass of 190 mm compared with the case of passing through the BK7 glass of 200 mm. Therefore, it is necessary to position each reference mirror further accordingly so as to equalize the total optical path length in the glass and air.

The combined lights that are respectively combined by the nine fiber couplers 103 enter the spectral processing portion 109.

In this embodiment, respective spectral processes of the nine lights are performed by the spectral optical system that uses nine sets of transmission gratings of 1,200 lines/mm and line sensors with a pixel pitch of 14 μm and 2,048 pixels, with the result that wavelength spectrum data containing interference signals is obtained.

A Fourier transformation process of the data is performed so that the OCT signals are obtained. Further, by synchronizing with the frequency of the galvano-scanner in the irradiation optical system 105, the OCT signals are obtained so that three-dimensional images of the retina 120 can be obtained.

The ocular lens used in this embodiment has a dispersion value that increases as being closer to the periphery, but depending on the used glass material, the dispersion value may decrease.

In addition, the BK7 glass is used as the dispersion compensation glass, but other glass material having a known wavelength dispersion value can be used.

In this case, the optical path length is also different, and hence it is necessary to adjust the position of the reference mirror group 108 again. In any case, according to the concept of the present invention, an appropriate dispersion compensation glass and an appropriate reference mirror position can be set in accordance with a distance from the optical axis of each light.

In this embodiment, a wavelength dispersion adjusting unit is disposed on the reference light side. However, the same function in the optical tomographic imaging apparatus of the present invention can be obtained also in the case where the wavelength dispersion adjusting unit is disposed on the measurement light side or on both sides.

Embodiment 2

In Embodiment 2, a structural example in which a light quantity adjusting unit is further added to the optical tomographic imaging apparatus of Embodiment 1 is described.

Figure 3:
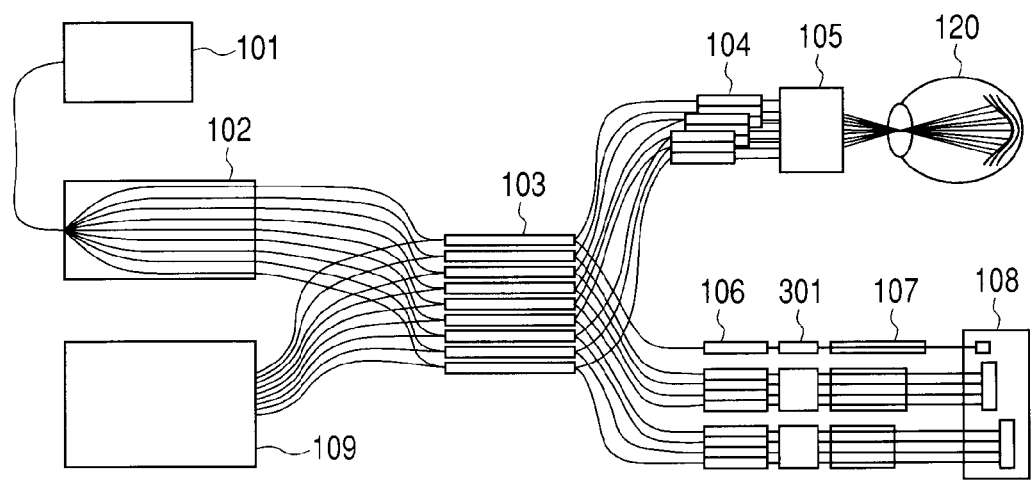
FIG. 3 is a diagram illustrating a structure of an optical tomographic imaging apparatus according to Embodiment 2 of the present invention.

FIG. 3 illustrates a structure of an optical tomographic imaging apparatus according to this embodiment.

Note that the components of FIG. 3 that are the same as the components of FIG. 1 are denoted by the same reference numerals, and hence redundant description thereof is omitted.

In Embodiment 1 described above, description is given of the structural example in which the reference mirror groups 108 for adjusting the optical path length and the BK7 glass materials 107 for dispersion compensation are put into three groups so as to reduce variation of the obtained OCT images.

In this embodiment, variation of sensitivity is reduced by providing a light quantity adjusting unit 301 for adjusting the light quantity of the nine lights.

The absorption rate of light from the low coherence light source 101 in the irradiation optical system 105 also varies in accordance with the distance from the optical axis of the light because of a difference of glass material similarly to Embodiment 1.

Therefore, three light quantity adjusting units 301 are respectively used for three groups of {F5}, {F2, F4, F6, F8}, and {F1, F3, F7, F9} similarly to Embodiment 1.

In this embodiment, a variable density filter is used as the light quantity adjusting unit 301. The variable density filter is obtained by vapor deposition of a metal thin film on a glass disk, so that the density varies continuously in the clockwise direction.

Therefore, by rotating the variable density filter, attenuation quantity of light can be delicately changed.

In this embodiment, three variable density filters are respectively disposed as the light quantity adjusting units 301 after the collimators 106 on the reference light side for producing the parallel light and before the BK7 glasses 107 for dispersion compensation. Confirming the OCT signals, the three variable density filters are rotated respectively, and the adjustment is performed so that variation of the entire signal decreases.

In this way, variation of sensitivity due to light quantity of the OCT signals of each light can be reduced.

A rotation type variable density filter is used in this embodiment, but a usual absorption or reflection type ND filter can be used instead of the variable type.

In accordance with necessary light attenuation quantity, an ND filter having a necessary optical density is selected or a plurality of ND filters are combined if necessary to be inserted at the position of the light quantity adjusting unit 301.

Instead of using the optical filter, it is possible to adopt a method of blocking a part of the light to thereby attenuate the light quantity, or a method of displacing the optical path by a glass plate to thereby attenuate coupling efficiency to the fiber collimator 106.

In addition, without limiting to the reference light side, even when the light quantity adjusting unit 301 is disposed on the measurement light side, the light source side, or the spectral processing portion side, the effect of the present invention can be obtained.

Embodiment 3

In Embodiment 3, a structural example in which a light sampling unit, a wave aberration measuring unit, and a wave aberration adjusting unit are further added to the optical tomographic imaging apparatus of Embodiment 2 is described.

Figure 4A:
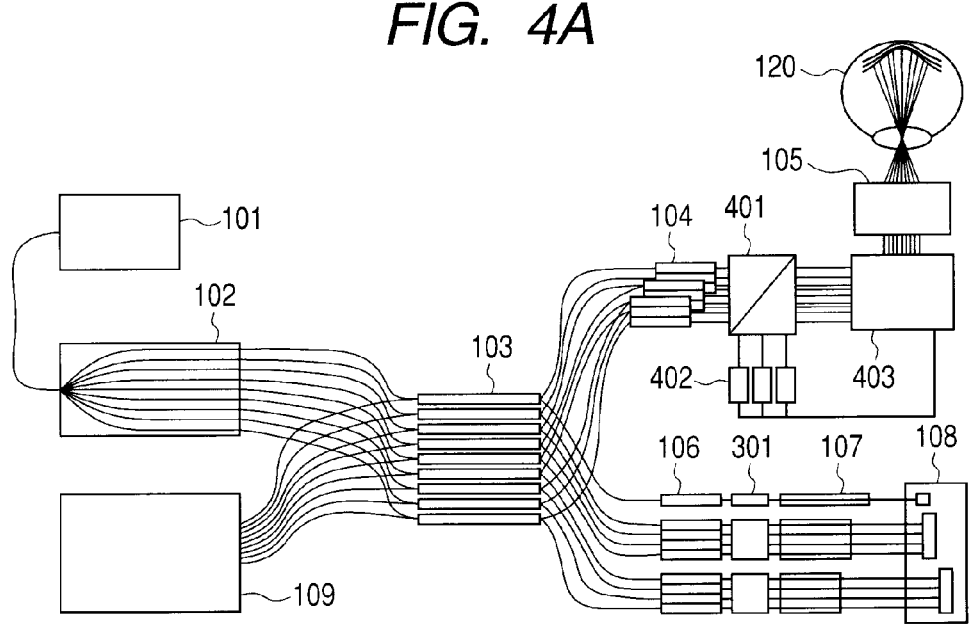
FIGS. 4A, 4B and 4C are diagrams illustrating a structure of an optical tomographic imaging apparatus according to Embodiment 3 of the present invention.
Figure 4B:
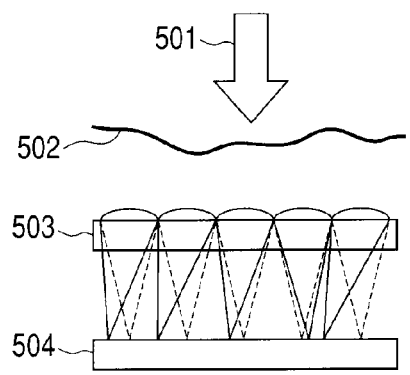
Figure 4C:
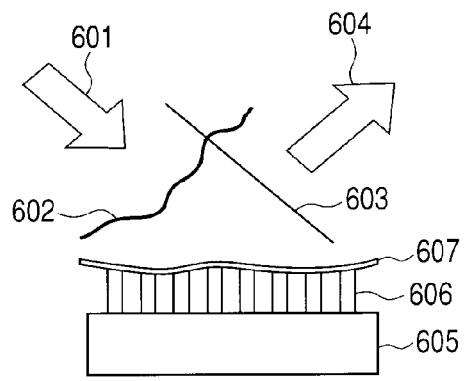

FIGS. 4A to 4C illustrate a structure of an optical tomographic imaging apparatus according to this embodiment.

Note that the components of FIGS. 4A to 4C that are the same as the components of FIGS. 1 and 3 are denoted by the same reference numerals, and hence redundant description thereof is omitted.

The optical tomographic imaging apparatus illustrated in FIG. 4A includes a light sampling unit 401, a wave aberration measuring unit 402, and a wave aberration adjusting unit 403.

In this embodiment, as illustrated in FIG. 4A, the light sampling unit 401, the wave aberration measuring unit 402, and the wave aberration adjusting unit 403 are further provided in the optical tomographic imaging apparatus of Embodiment 2, and hence the resolution of an image can further be improved.

The wave aberration includes spherical aberration, coma aberration, and astigmatic aberration, and the spherical aberration becomes particularly conspicuous as in the cases of Embodiments 1 and 2, in which a lens having a large numerical aperture (NA) is used for obtaining an OCT image having a wide angle of view.

This is because the spherical aberration is proportional to the cube of NA. If the spherical aberration is large, the light is refracted more as being farther from the optical axis, so as to cross the optical axis at a deviating position on the axis. As a result, the resolution and the SNR of the OCT image are deteriorated.

The light sampling unit 401 formed of the beam splitter is disposed between the fiber collimator 104 and the irradiation optical system 105.

The light sampling unit 401 causes a part of the measurement lights to branch and enter the wave aberration measuring unit 402, in which the wave aberration is measured.

FIG. 4B is a diagram illustrating a specific structure of the wave aberration measuring unit 402 of this embodiment.

In FIG. 4B, a light incident direction in the wave aberration measuring unit is represented by reference numeral 501 and an incident wavefront in the wave aberration measuring unit is represented by reference numeral 502, and the wave aberration measuring unit includes a lens array 503 and a sensor array 504. The light entering in the light incident direction 501 passes through the lens array 503 and is condensed onto the sensor array 504. If the incident light wavefront 502 is disturbed, the light is condensed at a position deviating from the optical axis of each lens array as illustrated not by the broken line but by the solid line. Therefore, the disturbance quantity of the wavefront can be measured from the deviation amount.

In this way, a wave aberration amount measured by the wave aberration measuring unit 402 is sent to the wave aberration adjusting unit 403 so that the wave aberration of each light is adjusted.

FIG. 4C illustrates a specific structure of the wave aberration adjusting unit 403 according to this embodiment.

In FIG. 4C, a light incident direction in the wave aberration adjusting unit is represented by reference numeral 601, an incident wavefront in the wave aberration adjusting unit is represented by reference numeral 602, and a corrected wavefront in the wave aberration adjusting unit is represented by reference numeral 603.

A light outgoing direction in the wave aberration adjusting unit is represented by reference numeral 604, and the wave aberration adjusting unit includes a wavefront adjustment mirror base 605, a wavefront adjustment mirror actuator 606, and a variable shape mirror 607.

Based on information that has already measured by the wave aberration measuring unit 402, the wavefront adjustment mirror actuator 606 disposed on the mirror base 605 is driven to deform the shape of the variable shape mirror 607 so that the disturbance of the wavefront is canceled.

The disturbance of the wavefront 602 of the light entering in the light incident direction 601 is canceled by the variable shape mirror 607, and hence the wave aberration of the corrected wavefront 603 of the light outgoing in the light outgoing direction 604 is reduced.

In Embodiment 3, similarly to Embodiments 1 and 2, the nine lights are divided into three groups having the same optical property. Therefore, the wave aberration measuring unit 402 measures only three typical lights representing the three groups, e.g., F5, F1, and F2.

In addition, in the same manner, the wave aberration adjusting units 403 can also be classified into three. Therefore, the aberration adjustment can be performed efficiently, and hence variation among lights can be reduced.

In addition, this embodiment describes the case where the wave aberration is adjusted, but the same is true for the case of other aberration such as image surface curvature.

Embodiment 4

In Embodiment 4, a structural example of the spectral processing portion is described.

Figure 5:
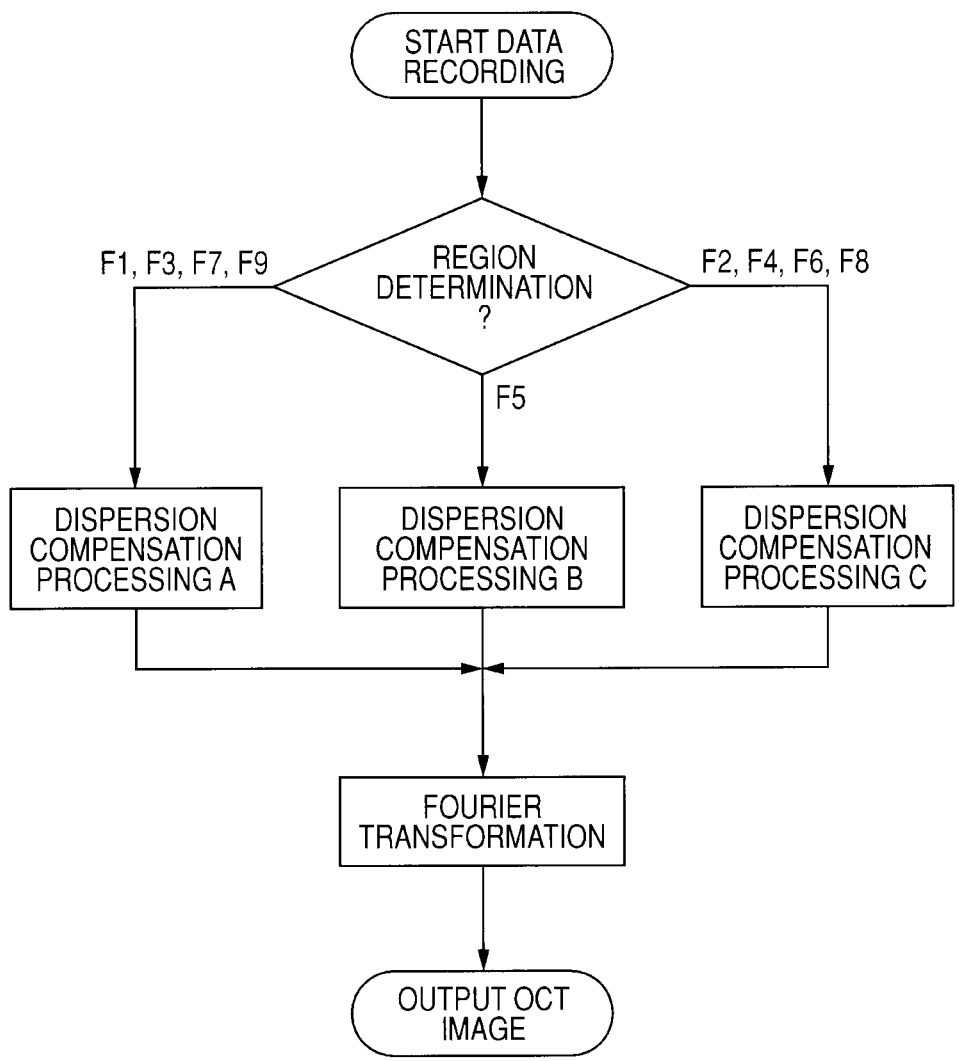
FIG. 5 is a diagram illustrating a procedure of spectral data processing by a data processing portion according to Embodiment 4 of the present invention.

FIG. 5 is a diagram illustrating a procedure of spectral data processing performed by a data processing portion according to this embodiment.

In Embodiments 1 to 3, the spectral processing of the nine combined lights entering the spectral processing portion 109 is performed by the method described in Embodiment 1, with the result that wavelength spectrum data containing the interference signals is obtained.

After that, the wavelength axis of the wavelength spectrum data is converted into wave number, and the OCT images are obtained through a step of high order dispersion compensation processing, a step of Fourier transformation process, and a step of integrating individual data so as to output the OCT images.

Generally, different correction parameters are used for nine lights so as to perform the data processing. Therefore, nine data processing steps are performed in parallel.

In contrast, in this embodiment, the spectral processing portion is configured such that the data processing portion can perform data processing by using a parameter for correcting the optical property in each group including lights having substantially the same distance from the optical axis.

For instance, a step of deciding a light measurement region is added after data recording, so as to include the data processing portion for performing the data processing by sharing a dispersion compensation parameter for each group having substantially the same distance from the optical axis.

Specifically, the process is performed by dividing it into three groups of {F5}, {F1, F3, F7, F9}, and {F2, F4, F6, F8}, and hence the dispersion compensation parameter is shared. Thus, dispersion compensation processing steps can be reduced to three steps.

Thus, the processing procedure is made to be efficient so that variation of the data processing can be reduced.

Note that this method can be applied to a system that uses a single light.

Here, considered is the case where the regions F1 to F9 in FIG. 2 are scanned by a single measurement light.

As described above, the obtained interference signals contains a dispersion amount that varies in accordance with an angle of view of the irradiation optical system.

It is supposed that the dispersion compensation is performed for the signals by a computing process. If the process is performed by a single parameter, good dispersion compensation is performed only for the signal from a particular region. In other regions, depth direction resolution remains deteriorated.

Therefore, concerning the signal obtained by measuring the entire region with a single light, as described above, a processing A with a certain parameter group is performed for the signals from the regions F1, F3, F7, and F9, while a processing B is performed with another parameter group for the region of F5.

In addition, a processing C is performed with a parameter group different from those of the processings A and B is performed in parallel for the regions of F2, F4, F6, and F8, and hence an appropriate dispersion compensation processing is performed for each region for securing the depth direction resolution in the entire region.

In the case of a single light, the number of regions is not limited unlike the case of division with respect to a plurality of lights. Therefore, a large number of regions can be set within a feasible computing process load, and hence a better dispersion compensation processing can be performed.

In addition, a single light is used here, but it is possible to use a plurality of lights and to further divide a region covered by each light, so as to set different parameters.

Embodiment 5

In Embodiment 5, a structural example of using a bulk optical system unlike Embodiments 1 to 4 that use the optical fiber is described.

Figure 6:
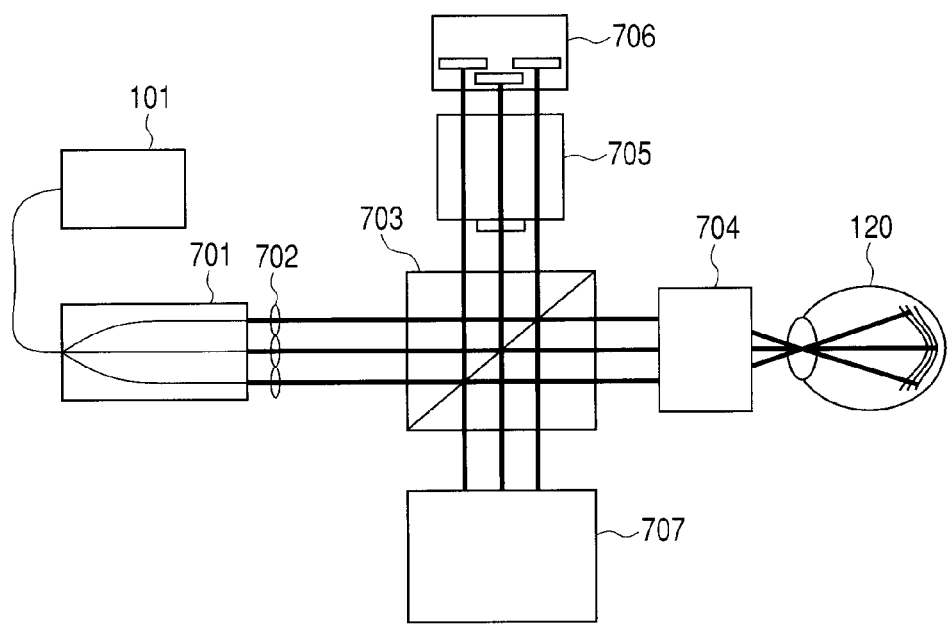
FIG. 6 is a diagram illustrating a structure of an optical tomographic imaging apparatus using a bulk optical system according to Embodiment 5 of the present invention.

FIG. 6 illustrates a structure of an optical tomographic imaging apparatus using a bulk optical system according to this embodiment.

Note that the components of FIG. 6 that are the same as the components of FIG. 1 are denoted by the same reference numeral, and hence redundant description thereof is omitted.

The optical tomographic imaging apparatus illustrated in FIG. 6 includes a trifurcation coupler 701, a collimate lens array 702, a cube beam splitter 703, an irradiation optical system 704, a dispersion compensation glass 705, a reference mirror unit 706, and a three-light spectral processing portion 707.

In this embodiment, a bulk optical system is used in contrast with Embodiments 1 to 4 in which the fiber optical system is used.

Specifically, in Embodiments 1 to 4, each of the following optical paths is constituted of an optical fiber: an optical path for directing the light from the light source to a position where the light is split into the measurement light and the reference light; an optical path for directing the measurement light to the object; an optical path for directing the reference light to the reference mirror; and an optical path for directing the interference light generated from the return light of the measurement light and the reference light reflected by the reference mirror to the spectral processing portion.

In contrast, this embodiment uses the bulk optical system. The output of the low coherence light source 101 is branched into three by the trifurcation coupler 701 and the three branched lights are converted to parallel lights by the collimate lens array 702.

Each of the three lights is split into the measurement light and the reference light by the 50:50 cube beam splitter 703.

The three measurement lights are condensed onto the retina 120 by the irradiation optical system 704 constituted of a galvano scanner, a scan lens, and an ocular lens.

The three lights are adjusted so that each of the regions F2, F5, and F8 of FIG. 2 is subjected to raster-scanning by a single light.

Scattered light from a condensing point of each of the three lights is directed to the cube beam splitter 703 via the irradiation optical system 704 and is combined with the reference lights.

On the other hand, the reference lights pass through the dispersion compensation glass 705 and are reflected by the reference mirror unit 706, so as to return to the cube beam splitter 703.

The irradiation optical system 704 uses the same ocular lens as Embodiment 1, and hence the length of the dispersion compensation glass can be 200 mm for {F5} and 195 mm for {F2, F8}.

Therefore, the dispersion compensation glass 705 can be a bonded structure of a wide BK7 glass having a length of 195 mm and a BK7 glass having a length of 5 mm which are bonded by applying a refractive index standard solution having the same refractive index as the BK7 glass.

Thus, the light for scanning the central region {F5} passes through the BK7 glass having a length of 200 mm, and the light for scanning the peripheral regions of {F2, F8} passes through the BK7 glass having a length of 195 mm.

The reference mirror unit 706 is constituted of three mirrors. Considering the length of the dispersion compensation glass, positions of the three mirrors are deviated and adjusted for matching with the optical path length of the measurement lights.

The scattered lights and the reference lights which are combined by the cube beam splitter 703 are directed to the three-light spectral processing portion 707 as they are, and the spectral process is performed similarly to Embodiment 1 so that the OCT signal is obtained.

Thus, the effect of the present invention can be proved also in the bulk optical system similarly to the fiber optical system.

Embodiment 6

Figure 7:
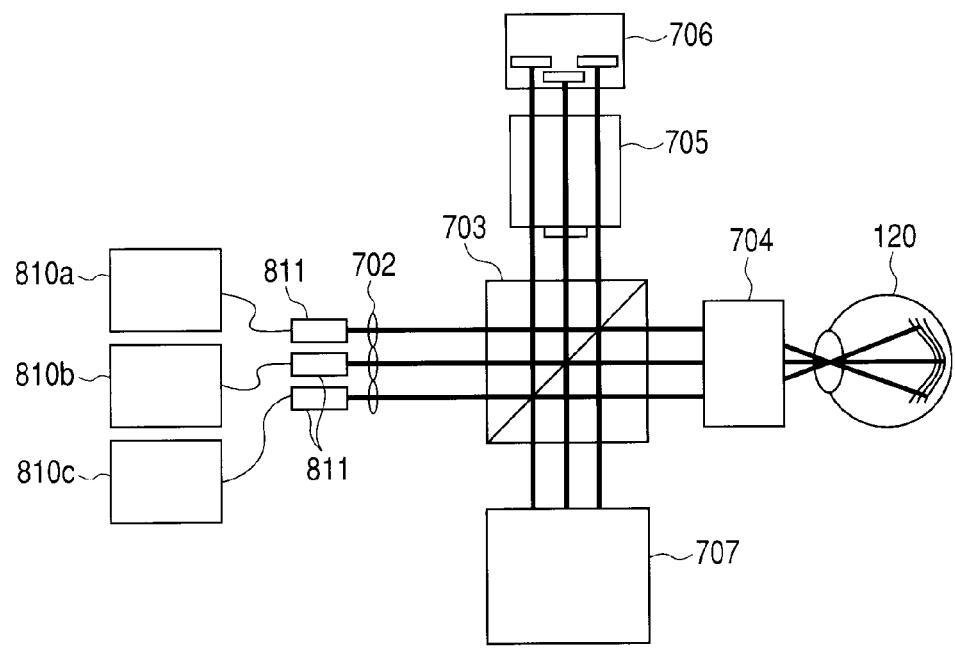
FIG. 7 is a diagram illustrating a structure of an optical tomographic imaging apparatus according to Embodiment 6 of the present invention.

FIG. 7 illustrated a structure of an optical tomographic imaging apparatus according to this embodiment.

Lights emitted from three SLD light sources 810a, 810b, and 810c go out from ends of optical fibers 811, respectively, and are converted to parallel lights by the collimate lens arrays 702. Concerning the other structures, the components that are the same as the components illustrated in FIG. 6 are denoted by the same reference numerals, and hence the redundant description thereof is omitted.

The effect of the present invention is valid also in the case where the different light sources are used for different lights as in this embodiment. In addition, this embodiment exemplifies the case of three lights, but the same effect can be obtained also in the case of two or more lights.

Embodiment 7

The embodiments described above exemplify the case where a Michelson type interferometer is used, while this embodiment describes a structural example in a case of a Mach-Zehnder type interferometer.

Figure 8:
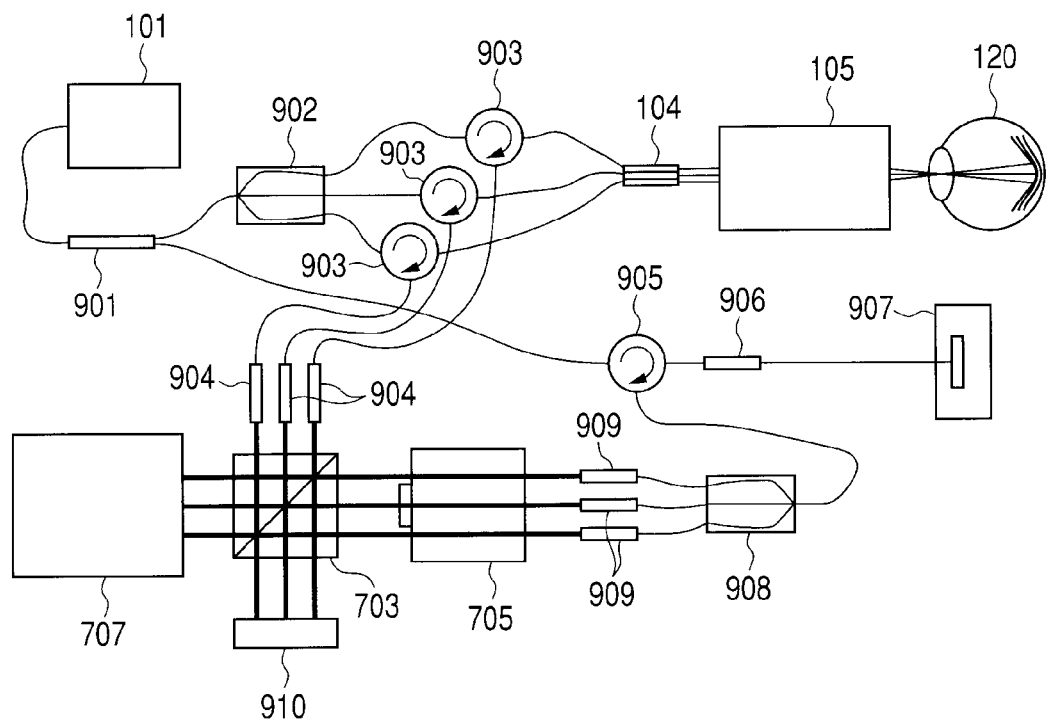
FIG. 8 is a diagram illustrating a structure of an optical tomographic imaging apparatus according to Embodiment 7 of the present invention.

FIG. 8 illustrates a structure of an optical tomographic imaging apparatus using a Mach-Zehnder type interferometer according to this embodiment.

Note that the components of FIG. 8 that are the same as the components illustrated in FIGS. 1 and 6 are denoted by the same reference numerals.

A light emitted from the SLD light source 101 is branched into a measurement light and a reference light by a 1:2 fiber beam splitter 901.

The measurement light is split equally into three lights by a 1:3 fiber beam splitter 902, and each of the lights enters a corresponding optical circulator 903.

The lights after passing through the optical circulators 903 are converted to parallel lights by the three fiber collimators 104, respectively, and are application onto the retina 120 of an eye by the irradiation optical system 105 constituted of a galvano scanner, a scan lens, and an ocular lens.

The three lights are adjusted to scan the same regions as in Embodiment 5.

Return lights reflected or scattered by the retina 120 pass through the same optical systems again and return to the optical circulators 903.

Due to the property of the optical circulators, the lights received by the optical circulators are output not to the fiber beam splitter 902 side but to the fiber collimator 904 side.

The return lights are converted to parallel lights by the fiber collimators 904 and enter the beam splitter 703.

The reference light passes through the optical circulator 905 and goes out from the fiber collimator 906. Then, the reference light is reflected by the reference mirror 907 and returns to the optical circulator 905.

The returning reflection light is output by the optical circulator 905 to a 1:3 fiber beam splitter 908, which splits the light equally into three lights. After that, the three lights are converted to parallel lights by the fiber collimators 909. Then, the parallel lights pass through the dispersion compensation glasses 705 and enter the beam splitter 703.

The three measurement lights entering the beam splitter 703 after scattered by the retina 120 and the three reference lights entering the beam splitter 703 after split equally into three are combined by the beam splitter 703 to be interference lights.

One group of the interference lights is directed to the three-light spectral processing portion 707 and the spectral process thereof is performed similarly to Embodiment 1 so that the OCT signal is obtained. The other group of the interference lights is not necessary and thus shielded by an aluminum plate 910 subjected to black alumite treatment.

As described above, the effect of the present invention is valid irrespective of the shape of an interferometer. In addition, this embodiment exemplifies the case of three lights, but the same effect can be obtained also in the case of two or more lights.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-332245, filed on Dec. 26, 2008, and Japanese Patent Application No. 2009-124105, filed on May 22, 2009, which are hereby incorporated by reference herein in their entirety.

The invention claimed is:

1. An optical tomographic imaging apparatus for obtaining at least a tomographic image of an object based on a plurality of interference lights obtained by interfering (a) a plurality of return lights from the object irradiated with a plurality of measurement lights and (b) a plurality of reference lights corresponding to the plurality of measurement lights, the apparatus comprising:
   an irradiation unit for irradiating the object with the plurality of measurement lights; and
   an optical property adjusting unit for adjusting an optical property of at least one of (a) the plurality of measurement lights, (b) the plurality of reference lights, and (c) the plurality of interference lights,
   wherein the plurality of measurement lights are divided into a plurality of groups, each group including measurement lights having substantially the same distance between an optical axis of the irradiation unit and that of each measurement light, and
   wherein the optical property adjusting unit applies the same adjusting method for at least one of (a) the measurement lights, (b) reference lights corresponding to the measurement lights, and (c) interference lights obtained by interfering (i) return lights from the object irradiated with the measurement lights and (ii) the reference lights, in a group of the plurality of groups, and applies a different adjusting method for a different group of the plurality of groups.

2. An optical tomographic imaging apparatus according to claim 1, wherein the optical property adjusting unit is one of:
   an adjusting unit disposed on a reference light side for adjusting an optical path length difference between the measurement lights and the reference lights;
   a compensating unit disposed on the reference light side for compensating for a wavelength dispersion difference between a measurement light side and the reference light side;
   a light quantity adjusting unit disposed on one of the reference light side, the measurement light side, a light source side, and a spectral processing portion side, for adjusting light quantity; and
   an adjusting unit disposed on the measurement light side for adjusting aberration of the irradiation optical system.

3. An optical tomographic imaging apparatus according to claim 2, wherein the spectral processing portion is a data processing portion for performing data processing by using a parameter for correcting the optical property for each group including measurement lights having substantially the same distance from the optical axis.

4. An optical tomographic imaging apparatus according to claim 3, wherein the data processing portion comprises a unit for performing data processing by sharing a parameter for dispersion compensation for each group including measurement lights having substantially the same distance from the optical axis.

5. An optical tomographic imaging apparatus according to claim 1, in which:
   an optical path for directing a light from a light source to a position where the light is split into the measurement lights and the reference lights,
   an optical path for directing the measurement lights to the object,
   an optical path for directing the reference lights to a reference mirror, and
   an optical path for directing the interference lights obtained by combining the return lights of the measurement lights and the reference lights reflected by the reference mirror to a spectral processing portion
   are each comprised of one of an optical fiber and a bulk.

6. A program for causing a computer to execute an imaging method using the optical tomographic imaging apparatus according to claim 1.

7. An optical tomographic imaging apparatus for obtaining at least a tomographic image of a subject's eye based on a plurality of interference lights obtained by interfering (a) a plurality of return lights from the subject's eye irradiated with a plurality of measurement lights and (b) a plurality of reference lights corresponding to the plurality of measurement lights, the apparatus comprising:
   an irradiation unit for irradiating an anterior ocular segment of the subject's eye with the plurality of measurement lights at mutually different angles; and
   an adjusting unit for adjusting optical properties of lights corresponding to the plurality of measurement lights, wherein the optical properties are based on a position and an angle at which the anterior ocular segment is irradiated with the plurality of measurement lights by the irradiation unit.

8. An optical tomographic imaging apparatus according to claim 7, wherein the irradiation unit irradiates the anterior ocular segment with the plurality of measurement lights through an objective lens, and
   wherein a distance between an optical axis of the objective lens and a region where the plurality of measurement lights passes through the objective lens corresponds to the position and the angle.

9. An optical tomographic imaging apparatus according to claim 8, wherein the adjusting unit is provided in common to optical paths of a reference light group corresponding to a measurement light group which is a part of the plurality of measurement lights and is classified based on a distance from the optical axis of the objective lens, and has a dispersion compensation unit for compensating a dispersion of a return light group corresponding to the reference light group.

10. An optical tomographic imaging apparatus according to claim 7, wherein the adjusting unit has a dispersion compensation unit for compensating a dispersion of the plurality of return lights, wherein the dispersion is based on a position and an angle at which the anterior ocular segment is irradiated with the plurality of measurement lights by the irradiation unit.

11. An optical tomographic imaging apparatus for obtaining at least a tomographic image of an object based on a plurality of interference lights obtained by interfering (a) a plurality of return lights from the object irradiated with a plurality of measurement lights with (b) a plurality of reference lights corresponding to the plurality of measurement lights, the apparatus comprising:

an irradiation unit configured to irradiate the object with the plurality of measurement lights; and an optical unit (a) disposed on optical paths of reference lights corresponding to measurement lights obtained by classifying the plurality of measurement lights based on a distance from an optical axis of the irradiation unit and (b) configured to be shared in common with respect to the reference lights, wherein at least one of the classifications of the plurality of measurement lights includes two or more measurement lights.

12. An optical tomographic imaging apparatus according to claim 11, further comprising a second optical unit that is different from the optical unit and that is disposed on optical paths of reference lights corresponding to measurement lights other than the obtained measurement lights.

13. An optical tomographic imaging apparatus according to claim 11, wherein the optical unit comprises one of the following units:

a dispersion compensation unit configured to compensate dispersions of return lights from the object irradiated with the obtained measurement lights and configured to be shared in common with respect to the reference lights;

an optical path length varying unit configured to vary optical path lengths of the reference lights and configured to be shared in common with respect to the reference lights; and a light quantity varying unit configured to vary light quantities of the reference lights and configured to be shared in common with respect to the reference lights.

14. An optical tomographic imaging apparatus according to claim 12, wherein the optical unit comprises one of the following units:

a dispersion compensation unit configured to compensate dispersions of return lights from the object irradiated with the obtained measurement lights and configured to be shared in common with respect to the reference lights;

an optical path length varying unit configured to vary optical path lengths of the reference lights and configured to be shared in common with respect to the reference lights; and a light quantity varying unit configured to vary light quantities of the reference lights and configured to be shared in common with respect to the reference lights.

15. An imaging apparatus for obtaining at least an image of an object based on a plurality of return lights from the object irradiated with a plurality of measurement lights, the apparatus comprising:

an irradiation unit configured to irradiate the object with the plurality of measurement lights; and a light quantity varying unit disposed on optical paths of measurement lights obtained by classifying the plurality of measurement lights based on a distance from an optical axis of the irradiation unit, the light quantity varying unit being configured to vary light quantities of the obtained measurement lights and being configured to be shared in common with respect to the obtained measurement lights.

16. An imaging apparatus according to claim 15, wherein the irradiation unit comprises a fiber beam splitter that provides the plurality of measurement lights.

17. An optical tomographic imaging apparatus comprising:

a scanning unit for scanning a measurement light on an object;

a processing unit for performing dispersion compensation by subjecting to a computing process an interference signal corresponding to an interference light obtained by interfering a return light from the object irradiated with the measurement light and a reference light corresponding to the measurement light according to a region where the measurement light is scanned on the object by the scanning unit; and an obtaining unit for obtaining a tomographic image of the object based on the interference signal subjected to the computing process.

18. An optical tomographic imaging apparatus according to claim 17, wherein, using a plurality of parameters respectively corresponding to measurement regions for the object that are classified into a plurality of groups, the processing unit performs the dispersion compensation by subjecting to the computing process the interference signal corresponding to the interference light from the measurement regions.

* * * * *